(12) United States Patent
Houghton et al.

(10) Patent No.: US 11,980,367 B2
(45) Date of Patent: May 14, 2024

(54) ANASTOMOSIS DEVICES

(71) Applicant: W. L. Gore & Associates, Inc., Newark, DE (US)

(72) Inventors: Michael J Houghton, Newark, DE (US); Sakthi Sambandam, Elkton, MD (US); Clifford P. Warner, West Chester, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 489 days.

(21) Appl. No.: 16/741,379

(22) Filed: Jan. 13, 2020

(65) Prior Publication Data

US 2020/0146680 A1 May 14, 2020

Related U.S. Application Data

(63) Continuation of application No. 14/700,427, filed on Apr. 30, 2015, now abandoned.
(Continued)

(51) Int. Cl.
| | |
|---|---|
| *A61B 17/11* | (2006.01) |
| *A61B 17/00* | (2006.01) |
| *A61F 2/06* | (2013.01) |
| *A61F 2/90* | (2013.01) |
| *A61B 17/064* | (2006.01) |

(Continued)

(52) U.S. Cl.
CPC ...... *A61B 17/1114* (2013.01); *A61B 17/0057* (2013.01); *A61B 17/11* (2013.01); *A61F 2/06* (2013.01); *A61F 2/90* (2013.01); *A61B 17/064* (2013.01); *A61B 2017/0641* (2013.01); *A61B 17/08* (2013.01); *A61B 17/083* (2013.01); *A61B 2017/1103* (2013.01); *A61B 2017/1107* (2013.01); *A61B 2017/1132* (2013.01);
(Continued)

(58) Field of Classification Search
CPC . A61B 17/1114; A61B 17/0057; A61B 17/11; A61F 2/06; A61F 2/90; A61F 2002/077
See application file for complete search history.

(56) References Cited

U.S. PATENT DOCUMENTS

| | | | |
|---|---|---|---|
| 3,818,511 A | 6/1974 | Goldberg et al. | |
| 4,119,100 A | 10/1978 | Rickett | |

(Continued)

FOREIGN PATENT DOCUMENTS

| | | |
|---|---|---|
| CN | 101374477 A | 2/2009 |
| CN | 201379668 Y | 1/2010 |

(Continued)

OTHER PUBLICATIONS

European Search Report from 15721986.6 dated Dec. 12, 2017, 4 pages.
(Continued)

*Primary Examiner* — Phong Son H Dang

(57) ABSTRACT

Implantable medical devices for connecting tissue layers, such as for connecting a gallbladder and a portion of a gastrointestinal tract to create an anastomosis, include a tubular structure having a plurality of apposition portions, a central region, and a covering material. The methods of using the devices include endoscopic deployment, and the devices may include self-expanding frameworks that facilitate a secure connection between the tissue structures.

13 Claims, 7 Drawing Sheets

Related U.S. Application Data

(60) Provisional application No. 61/987,954, filed on May 2, 2014.

(51) Int. Cl.
*A61B 17/08* (2006.01)
*A61F 2/07* (2013.01)

(52) U.S. Cl.
CPC ............... *A61B 2017/1135* (2013.01); *A61B 2017/1139* (2013.01); *A61F 2002/077* (2013.01)

(56) References Cited

U.S. PATENT DOCUMENTS

| | | | |
|---|---|---|---|
| 4,338,937 A | 7/1982 | Lerman | |
| 4,381,765 A | 5/1983 | Burton | |
| 5,171,259 A | 12/1992 | Inoue | |
| 5,224,953 A | 7/1993 | Morgentaler | |
| 5,261,898 A | 11/1993 | Polin et al. | |
| 5,354,308 A | 10/1994 | Simon et al. | |
| 5,562,728 A | 10/1996 | Lazarus et al. | |
| 5,741,297 A | 4/1998 | Simon | |
| 5,755,778 A | 5/1998 | Kleshinski | |
| 5,797,933 A | 8/1998 | Snow et al. | |
| 5,824,041 A | 10/1998 | Lenker et al. | |
| 5,830,222 A | 11/1998 | Makower | |
| 5,868,783 A | 2/1999 | Tower | |
| 5,945,994 A | 8/1999 | Shimizu et al. | |
| 5,957,949 A | 9/1999 | Leonhardt et al. | |
| 6,007,544 A | 12/1999 | Kim | |
| 6,077,291 A | 6/2000 | Das | |
| 6,120,534 A | 9/2000 | Ruiz | |
| 6,165,209 A | 12/2000 | Patterson et al. | |
| 6,168,621 B1 | 1/2001 | Vrba | |
| 6,171,329 B1 | 1/2001 | Shaw et al. | |
| 6,193,734 B1 | 2/2001 | Bolduc et al. | |
| 6,214,029 B1 | 4/2001 | Thill et al. | |
| 6,217,608 B1 | 4/2001 | Penn et al. | |
| 6,290,728 B1 | 9/2001 | Phelps et al. | |
| 6,315,708 B1 | 11/2001 | Salmon et al. | |
| 6,315,792 B1 | 11/2001 | Armstrong et al. | |
| 6,355,052 B1 | 3/2002 | Neuss et al. | |
| 6,391,036 B1 | 5/2002 | Berg et al. | |
| 6,391,039 B1 | 5/2002 | Nicholas et al. | |
| 6,416,543 B1 | 7/2002 | Hilaire et al. | |
| 6,419,681 B1 | 7/2002 | Vargas et al. | |
| 6,432,127 B1 | 8/2002 | Kim et al. | |
| 6,468,303 B1 | 10/2002 | Amplatz et al. | |
| 6,485,496 B1 | 11/2002 | Suyker et al. | |
| 6,485,507 B1 | 11/2002 | Walak et al. | |
| 6,488,702 B1 | 12/2002 | Besselink | |
| 6,579,314 B1 | 6/2003 | Lombardi et al. | |
| 6,585,758 B1 | 7/2003 | Chouinard et al. | |
| 6,616,675 B1 | 9/2003 | Evard et al. | |
| 6,629,992 B2 | 10/2003 | Bigus et al. | |
| 6,666,883 B1 | 12/2003 | Seguin et al. | |
| 6,712,836 B1 | 3/2004 | Berg et al. | |
| 6,863,684 B2 | 3/2005 | Kim et al. | |
| 6,866,674 B2 | 3/2005 | Galdonik et al. | |
| 6,911,037 B2 | 6/2005 | Gainor et al. | |
| 6,945,994 B2 | 9/2005 | Austin et al. | |
| 6,958,037 B2 | 10/2005 | Ewers et al. | |
| 7,022,131 B1 | 4/2006 | Derowe et al. | |
| 7,025,777 B2 | 4/2006 | Moore | |
| 7,029,482 B1 | 4/2006 | Vargas et al. | |
| 7,037,344 B2 | 5/2006 | Kagan et al. | |
| 7,115,136 B2 | 10/2006 | Park et al. | |
| 7,182,771 B1 | 2/2007 | Houser et al. | |
| 7,223,274 B2 | 5/2007 | Vargas et al. | |
| 7,252,680 B2 | 8/2007 | Freitag | |
| 7,303,569 B2 | 12/2007 | Yencho et al. | |
| 7,431,729 B2 | 10/2008 | Chanduszko | |
| 7,527,644 B2 | 5/2009 | Mangiardi et al. | |
| 7,547,321 B2 | 6/2009 | Silvestri et al. | |
| 7,585,306 B2 | 9/2009 | Abbott et al. | |
| 7,608,086 B2 | 10/2009 | Tanaka et al. | |
| 7,632,302 B2 | 12/2009 | Vreeman et al. | |
| 7,780,686 B2 | 8/2010 | Park et al. | |
| 7,828,814 B2 | 11/2010 | Brenneman et al. | |
| 7,892,247 B2 | 2/2011 | Conston et al. | |
| 7,901,430 B2 | 3/2011 | Matsuura et al. | |
| 8,029,534 B2 | 10/2011 | Hruska et al. | |
| 8,043,360 B2 | 10/2011 | Mcnamara et al. | |
| 8,109,946 B2 | 2/2012 | Cahill et al. | |
| 8,114,125 B2 | 2/2012 | Seibold et al. | |
| 8,197,498 B2 | 6/2012 | Coleman et al. | |
| 8,257,389 B2 | 9/2012 | Chanduszko et al. | |
| 8,262,691 B2 | 9/2012 | Mcguckin et al. | |
| 8,343,088 B2 | 1/2013 | Bates et al. | |
| 8,398,676 B2 | 3/2013 | Roorda et al. | |
| 8,409,167 B2 * | 4/2013 | Roschak | A61M 29/02 604/506 |
| 8,425,539 B2 | 4/2013 | Binmoeller et al. | |
| 8,430,934 B2 | 4/2013 | Das | |
| 8,435,284 B2 | 5/2013 | Eidenschink et al. | |
| 8,454,632 B2 | 6/2013 | Binmoeller et al. | |
| 8,579,935 B2 | 11/2013 | Devries et al. | |
| 8,641,747 B2 | 2/2014 | Brenneman et al. | |
| 8,679,171 B2 | 3/2014 | Deem et al. | |
| 8,728,155 B2 | 5/2014 | Montorfano et al. | |
| 8,740,940 B2 | 6/2014 | Maahs et al. | |
| 8,864,813 B2 | 10/2014 | Barr | |
| 8,870,916 B2 | 10/2014 | Ewers et al. | |
| 8,992,604 B2 | 3/2015 | Gross et al. | |
| 9,597,204 B2 | 3/2017 | Benary et al. | |
| 9,668,853 B2 | 6/2017 | Shin | |
| 9,782,533 B2 | 10/2017 | Brenneman et al. | |
| 9,993,251 B2 | 6/2018 | Todd et al. | |
| 10,004,509 B2 | 6/2018 | Todd | |
| 10,363,040 B2 | 7/2019 | Sambandam | |
| 10,806,458 B2 | 10/2020 | Todd | |
| 11,596,409 B2 | 3/2023 | Todd | |
| 11,712,230 B2 | 8/2023 | Johnson et al. | |
| 11,724,075 B2 | 8/2023 | Johnson | |
| 2001/0021872 A1 | 9/2001 | Bailey et al. | |
| 2001/0047180 A1 * | 11/2001 | Grudem | A61B 17/11 606/153 |
| 2002/0082627 A1 | 6/2002 | Berg et al. | |
| 2002/0099431 A1 | 7/2002 | Armstrong et al. | |
| 2002/0099437 A1 | 7/2002 | Anson et al. | |
| 2002/0161341 A1 | 10/2002 | Stinson et al. | |
| 2002/0169475 A1 | 11/2002 | Gainor et al. | |
| 2002/0183787 A1 | 12/2002 | Wahr et al. | |
| 2003/0028213 A1 | 2/2003 | Thill et al. | |
| 2003/0032967 A1 | 2/2003 | Park et al. | |
| 2003/0055441 A1 | 3/2003 | Suyker et al. | |
| 2003/0069533 A1 | 4/2003 | Kakutani et al. | |
| 2003/0093096 A1 | 5/2003 | Mcguckin et al. | |
| 2003/0109893 A1 * | 6/2003 | Vargas | A61B 17/32053 606/153 |
| 2003/0120292 A1 * | 6/2003 | Park | A61B 17/083 606/153 |
| 2003/0139819 A1 | 7/2003 | Beer et al. | |
| 2003/0144578 A1 * | 7/2003 | Koster, Jr. | A61B 17/11 600/155 |
| 2003/0191482 A1 | 10/2003 | Suyker et al. | |
| 2003/0225421 A1 | 12/2003 | Peavey et al. | |
| 2004/0073242 A1 | 4/2004 | Chanduszko | |
| 2004/0078053 A1 | 4/2004 | Berg et al. | |
| 2004/0092977 A1 | 5/2004 | Vargas et al. | |
| 2004/0098105 A1 | 5/2004 | Stinson et al. | |
| 2004/0133236 A1 | 7/2004 | Chanduszko | |
| 2004/0204755 A1 * | 10/2004 | Robin | A61F 2/07 623/1.21 |
| 2004/0211433 A1 | 10/2004 | Albright | |
| 2005/0049675 A1 | 3/2005 | Wallace | |
| 2005/0055082 A1 | 3/2005 | Ben Muvhar et al. | |
| 2005/0070934 A1 | 3/2005 | Tanaka et al. | |
| 2005/0070935 A1 | 3/2005 | Ortiz | |
| 2005/0070957 A1 | 3/2005 | Das | |
| 2005/0149071 A1 | 7/2005 | Abbott et al. | |
| 2005/0154465 A1 | 7/2005 | Hodges et al. | |
| 2005/0228413 A1 | 10/2005 | Binmoeller et al. | |

(56) References Cited

U.S. PATENT DOCUMENTS

| | | |
|---|---|---|
| 2005/0234509 A1 | 10/2005 | Widomski et al. |
| 2005/0251201 A1 | 11/2005 | Roue et al. |
| 2005/0273124 A1 | 12/2005 | Chanduszko |
| 2005/0288786 A1 | 12/2005 | Chanduszko |
| 2006/0047337 A1 | 3/2006 | Brenneman |
| 2006/0052821 A1 | 3/2006 | Abbott et al. |
| 2006/0106418 A1 | 5/2006 | Seibold et al. |
| 2006/0200228 A1 | 9/2006 | Penn et al. |
| 2006/0212055 A1 | 9/2006 | Karabey et al. |
| 2006/0217761 A1 | 9/2006 | Opolski |
| 2007/0055358 A1 | 3/2007 | Krolik et al. |
| 2007/0073337 A1 | 3/2007 | Abbott et al. |
| 2007/0123917 A1 | 5/2007 | Ortiz et al. |
| 2007/0168014 A1 | 7/2007 | Jimenez et al. |
| 2007/0244518 A1 | 10/2007 | Callaghan |
| 2007/0249985 A1 | 10/2007 | Brenneman et al. |
| 2007/0282430 A1 | 12/2007 | Thommen et al. |
| 2007/0283552 A1 | 12/2007 | Gale et al. |
| 2008/0086168 A1 | 4/2008 | Cahill |
| 2008/0091235 A1 | 4/2008 | Sirota |
| 2008/0243151 A1 | 10/2008 | Binmoeller et al. |
| 2008/0262518 A1 | 10/2008 | Freudenthal |
| 2009/0076541 A1 | 3/2009 | Chin et al. |
| 2009/0090366 A1 | 4/2009 | Cuevas et al. |
| 2009/0093873 A1* | 4/2009 | Navia ............... A61F 2/07 623/1.36 |
| 2009/0118745 A1 | 5/2009 | Paul, Jr. |
| 2009/0143713 A1 | 6/2009 | Van et al. |
| 2009/0187240 A1 | 7/2009 | Clerc et al. |
| 2009/0228038 A1 | 9/2009 | Amin |
| 2009/0281557 A1 | 11/2009 | Sander et al. |
| 2010/0010520 A1 | 1/2010 | Takahashi et al. |
| 2010/0023132 A1 | 1/2010 | Imran |
| 2010/0036401 A1* | 2/2010 | Navia ............... A61F 2/064 606/155 |
| 2010/0100105 A1 | 4/2010 | Bates et al. |
| 2010/0106171 A1 | 4/2010 | Arepally et al. |
| 2010/0114128 A1 | 5/2010 | Coleman et al. |
| 2010/0114290 A1 | 5/2010 | Rasmussen et al. |
| 2010/0130995 A1 | 5/2010 | Yevzlin et al. |
| 2010/0174253 A1 | 7/2010 | Cline et al. |
| 2010/0234878 A1 | 9/2010 | Hruska et al. |
| 2010/0268316 A1 | 10/2010 | Brenneman et al. |
| 2010/0305590 A1 | 12/2010 | Holmes et al. |
| 2011/0040366 A1 | 2/2011 | Goetz et al. |
| 2011/0054381 A1 | 3/2011 | Van et al. |
| 2011/0060398 A1 | 3/2011 | Tupil et al. |
| 2011/0118765 A1 | 5/2011 | Aguirre |
| 2011/0125244 A1 | 5/2011 | Roeder et al. |
| 2011/0137410 A1 | 6/2011 | Hacohen |
| 2011/0213415 A1 | 9/2011 | Mcguckin et al. |
| 2011/0218609 A1 | 9/2011 | Chobotov et al. |
| 2011/0257461 A1 | 10/2011 | Lipperman et al. |
| 2011/0257723 A1 | 10/2011 | Mcnamara |
| 2011/0301689 A1 | 12/2011 | Dorn et al. |
| 2012/0065652 A1 | 3/2012 | Cully et al. |
| 2012/0089216 A1 | 4/2012 | Rapaport et al. |
| 2012/0130417 A1 | 5/2012 | Lepulu et al. |
| 2012/0172927 A1 | 7/2012 | Campbell et al. |
| 2012/0232505 A1 | 9/2012 | Eskaros et al. |
| 2012/0241503 A1 | 9/2012 | Baxter, III et al. |
| 2013/0012969 A1 | 1/2013 | Shin |
| 2013/0030351 A1 | 1/2013 | Belhe et al. |
| 2013/0030521 A1 | 1/2013 | Nitzan et al. |
| 2013/0041451 A1 | 2/2013 | Patterson et al. |
| 2013/0053784 A1 | 2/2013 | Houser et al. |
| 2013/0096606 A1 | 4/2013 | Bruchman et al. |
| 2013/0165967 A1 | 6/2013 | Amin et al. |
| 2013/0197623 A1* | 8/2013 | McHugo ............... A61F 2/885 623/1.22 |
| 2013/0218192 A1 | 8/2013 | Erzberger et al. |
| 2013/0245742 A1 | 9/2013 | Norris |
| 2013/0261531 A1 | 10/2013 | Gallagher et al. |
| 2013/0317546 A1 | 11/2013 | Brown |
| 2014/0012368 A1 | 1/2014 | Sugimoto et al. |
| 2014/0031842 A1 | 1/2014 | Brenneman et al. |
| 2014/0074155 A1 | 3/2014 | Rothstein et al. |
| 2014/0236064 A1 | 8/2014 | Binmoeller et al. |
| 2014/0303710 A1 | 10/2014 | Zhang et al. |
| 2014/0343602 A1 | 11/2014 | Cox et al. |
| 2015/0005810 A1 | 1/2015 | Center et al. |
| 2015/0066077 A1 | 3/2015 | Akpinar |
| 2015/0250630 A1 | 9/2015 | Irwin et al. |
| 2015/0265437 A1 | 9/2015 | Fleury et al. |
| 2015/0313595 A1 | 11/2015 | Houghton et al. |
| 2015/0313598 A1* | 11/2015 | Todd ............... A61B 17/11 606/153 |
| 2015/0313599 A1 | 11/2015 | Johnson et al. |
| 2016/0045199 A1 | 2/2016 | Mooney |
| 2016/0074023 A1 | 3/2016 | Sakamoto et al. |
| 2016/0135813 A1 | 5/2016 | Johnson et al. |
| 2016/0256169 A1 | 9/2016 | Ben-Muvhar et al. |
| 2017/0020498 A1 | 1/2017 | Blom |
| 2017/0105854 A1* | 4/2017 | Treacy ............... A61F 2/88 |
| 2018/0221194 A1 | 8/2018 | Eskaros et al. |
| 2018/0242972 A1 | 8/2018 | Todd |
| 2018/0250009 A1 | 9/2018 | Todd et al. |
| 2018/0296809 A1 | 10/2018 | Johnson |
| 2019/0298909 A1 | 10/2019 | Cully et al. |
| 2020/0015823 A1 | 1/2020 | Sambandam |
| 2020/0146680 A1 | 5/2020 | Houghton et al. |
| 2021/0085328 A1 | 3/2021 | Todd |
| 2022/0370071 A1 | 11/2022 | Johnson et al. |
| 2023/0255632 A1 | 8/2023 | Todd |

FOREIGN PATENT DOCUMENTS

| | | |
|---|---|---|
| CN | 101951983 A | 1/2011 |
| CN | 102083391 A | 6/2011 |
| CN | 102395323 A | 3/2012 |
| CN | 102802539 A | 11/2012 |
| CN | 202801864 U | 3/2013 |
| CN | 103200975 A | 7/2013 |
| CN | 103209649 A | 7/2013 |
| CN | 103313681 A | 9/2013 |
| CN | 103598902 A | 2/2014 |
| CN | 103945775 A | 7/2014 |
| CN | 104168839 A | 11/2014 |
| CN | 104519838 A | 4/2015 |
| CN | 104968284 A | 10/2015 |
| CN | 106413586 A | 2/2017 |
| DE | 10148185 A1 | 4/2003 |
| EP | 0991375 A1 | 4/2000 |
| EP | 1790297 A1 | 5/2007 |
| EP | 1480565 B1 | 12/2008 |
| EP | 2543323 A1 | 1/2013 |
| EP | 3136982 A2 | 3/2017 |
| EP | 3136984 A1 | 3/2017 |
| GB | 2409978 A | 7/2005 |
| IN | 104244843 A | 12/2014 |
| JP | 2000-505316 A | 5/2000 |
| JP | 2001-501493 A | 2/2001 |
| JP | 2001-520908 A | 11/2001 |
| JP | 2001-340346 A | 12/2001 |
| JP | 2003-527939 A | 9/2003 |
| JP | 2004-049806 A | 2/2004 |
| JP | 2005-503881 A | 2/2005 |
| JP | 2005-518863 A | 6/2005 |
| JP | 2005-528181 A | 9/2005 |
| JP | 2005-534390 A | 11/2005 |
| JP | 2006-006648 A | 1/2006 |
| JP | 2007-530128 A | 11/2007 |
| JP | 2009-508641 A | 3/2009 |
| JP | 2009-518149 A | 5/2009 |
| JP | 2010-523209 A | 7/2010 |
| JP | 2010-528821 A | 8/2010 |
| JP | 2011-509758 A | 3/2011 |
| JP | 2011-519709 A | 7/2011 |
| JP | 2013-013715 A | 1/2013 |
| JP | 2014-503246 A | 2/2014 |
| JP | 2015-500665 A | 1/2015 |
| JP | 2021-155586 A | 10/2021 |
| JP | 2021-192846 A | 12/2021 |
| WO | 97/27898 A1 | 8/1997 |

(56) References Cited

FOREIGN PATENT DOCUMENTS

| | | |
|---|---|---|
| WO | 97/32543 A1 | 9/1997 |
| WO | 98/02099 A1 | 1/1998 |
| WO | 98/08462 A2 | 3/1998 |
| WO | 98/16174 A1 | 4/1998 |
| WO | 98/58600 A1 | 12/1998 |
| WO | 01/72367 A1 | 10/2001 |
| WO | 2003/028522 A2 | 4/2003 |
| WO | 03/73944 A1 | 9/2003 |
| WO | 2003/103476 A2 | 12/2003 |
| WO | 2004/012603 A2 | 2/2004 |
| WO | 2004/087236 A2 | 10/2004 |
| WO | 2005/089655 A1 | 9/2005 |
| WO | 2006/121855 A2 | 11/2006 |
| WO | 2007/024964 A1 | 3/2007 |
| WO | 2007/053243 A2 | 5/2007 |
| WO | 2007/100970 A2 | 9/2007 |
| WO | 2008/157172 A1 | 12/2008 |
| WO | 2009/082718 A1 | 7/2009 |
| WO | 2009/091899 A2 | 7/2009 |
| WO | 2009/109348 A1 | 9/2009 |
| WO | 2009/140195 A1 | 11/2009 |
| WO | 2009/146369 A1 | 12/2009 |
| WO | 2010/129162 A1 | 11/2010 |
| WO | 2012/034108 A1 | 3/2012 |
| WO | 2012/067912 A1 | 5/2012 |
| WO | 2012/071075 A1 | 5/2012 |
| WO | 2013/152891 A2 | 10/2013 |
| WO | 2015/168501 A2 | 11/2015 |
| WO | 2015/168504 A2 | 11/2015 |
| WO | 2015/168506 A1 | 11/2015 |
| WO | 2015/168507 A1 | 11/2015 |
| WO | 2015/168508 A2 | 11/2015 |

OTHER PUBLICATIONS

Extended European Search Report from EP18161679.8, dated Jun. 20, 2018, 7 pages.
International Preliminary Report on Patentability received for PCT Patent Application No. PCT/US15/28711, dated Nov. 17, 2016, 11 pages.
International Preliminary Report on Patentability received for PCT Patent Application No. PCT/US15/28715, dated Nov. 17, 2016, 8 pages.
International Preliminary Report on Patentability received for PCT Patent Application No. PCT/US15/28717, dated Nov. 17, 2016, 9 pages.
International Preliminary Report on Patentability received for PCT Patent Application No. PCT/US15/28721, dated Nov. 17, 2016, 8 pages.
International Preliminary Report on Patentability received for PCT Patent Application No. PCT/US2015/028707, dated Nov. 17, 2016, 12 pages.
International Preliminary Report on Patentability received for PCT Patent Application No. PCT/US2016/055255, dated May 11, 2018, 7 pages.
International Preliminary Report on Patentability received for PCT Patent Application No. PCT/US2018/028120, dated Oct. 31, 2019, 10 pages.
International Search Report and Written Opinion from PCT/US2012/027984, dated Jun. 6, 2012, 11 pages.
International Search Report and Written Opinion from PCT/US2015/028707, dated Oct. 23, 2015, 19 pages.
International Search Report and Written Opinion from PCT/US2015/028711, completed Jan. 20, 2016, 17 pages.
International Search Report and Written Opinion from PCT/US2015/028721, dated Oct. 28, 2015, 13 pages.
International Search Report and Written Opinion from PCT/US2018/028120, dated Aug. 21, 2018, 17 pages.
International Search Report and Written Opinion received for PCT Patent Application No. PCT/US15/28711, dated Feb. 1, 2016, 17 pages.
International Search Report and Written Opinion received for PCT Patent Application No. PCT/US15/28715, dated Aug. 25, 2015, 12 pages.
International Search Report and Written Opinion received for PCT Patent Application No. PCT/US15/28717, dated Aug. 26, 2015, 13 pages.
International Search Report and Written Opinion received for PCT Patent Application No. PCT/US2015/028707, dated Oct. 23, 2015, 19 pages.
International Search Report and Written Opinion received for PCT Patent Application No. PCT/US2016/055255, dated Jan. 20, 2017, 8 pages.
International Search Report for PCT/US2016/055255 dated Dec. 20, 2016 and dated Jan. 20, 2017.

* cited by examiner

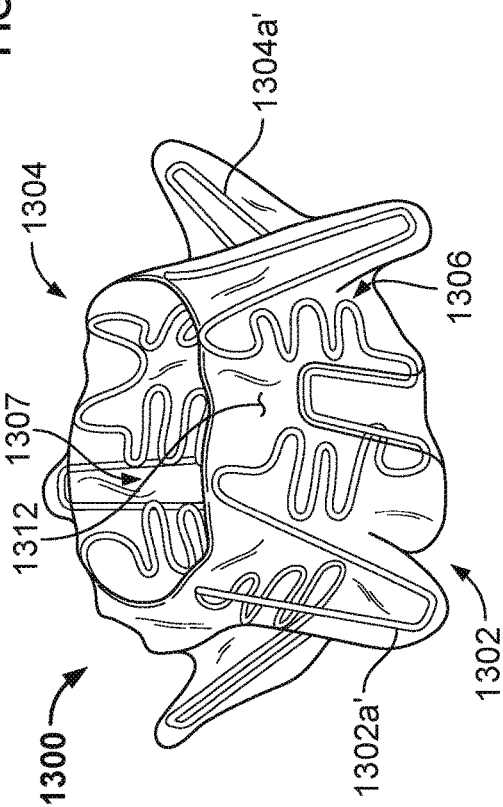
FIG. 11
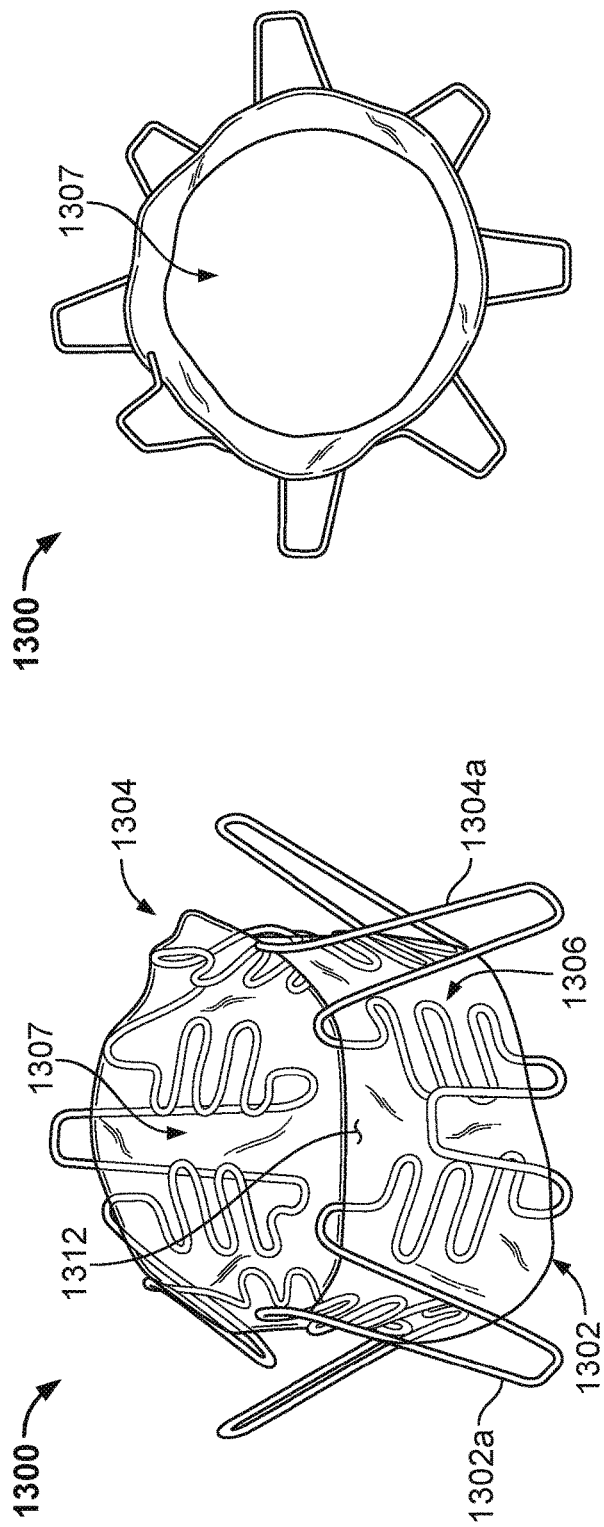
FIG. 10
FIG. 12

ANASTOMOSIS DEVICES

CROSS-REFERENCE TO RELATED APPLICATION

This application is a continuation of U.S. patent application Ser. No. 14/700,427, filed Apr. 30, 2015, which claims the benefit of U.S. Provisional Application 61/987,954, filed May 2, 2014, both of which are incorporated herein by reference in their entireties for all purposes.

FIELD

The present disclosure relates generally to implantable medical devices, and more specifically, to implantable devices for connecting tissue layers to create an anastomosis. Methods for using the implantable medical devices are also disclosed.

BACKGROUND

An anastomosis is a cross-connection between two tissue structures, such as blood vessels or intestines. For example, in the context of coronary artery bypass graft surgery, a graft vessel is anastomosed to a native coronary artery so that blood can flow through the graft vessel.

Anastomoses can be created in various manners including, but not limited to: end-to-end, end-to-side, and side-to-side anastomoses. Often, suturing is used to create such anastomoses.

SUMMARY

One aspect of the invention relates to a medical device that includes (1) an expandable frame having a first end, a second end, and a middle portion between the first end and the second end, (2) a first apposition portion including a plurality of first apposition members, each of the first apposition members extending toward the middle portion, and (3) a second apposition portion including a plurality of second apposition members each of the second apposition members extending toward the middle portion. A first portion of each of the first apposition members may be oriented at a first angle in relation to a surface of the middle portion and a second portion of each of the first apposition members may be oriented at a second angle in relation to the surface of the middle portion. In exemplary embodiments, the first angle is acute and is less than the second angle. Also, a first portion of each of the second apposition members may be oriented at a third angle in relation to the surface of the middle portion and a second portion of each of the second apposition members may be oriented at a fourth angle in relation to the surface of the middle portion. In exemplary embodiments, the third angle is acute and is less than the fourth angle. In some embodiments, at least one the first apposition members is longer than one or more others of the first apposition members. Additionally, at least one of the first apposition members may be longer than at least one of the second apposition members. In one or more embodiment, all of the first apposition members are longer than all of the second apposition members. The first apposition members may or may not be in axial alignment with the second apposition members. In another embodiment, one or more of the first apposition members may longitudinally overlap with one or more of the second apposition members. A cover material may be positioned on at least a portion of the frame.

A second aspect of the invention relates to a medical device that includes a frame including an elongate member defining (1) a first apposition portion that includes one or more first flange members configured to contact a first tissue surface and to provide an apposition force against the first tissue surface, (2) a second apposition portion that includes one or more second flange members configured to contact a second tissue surface and to provide an apposition force against the second tissue surface, and (3) a central portion having a first end and a second end where the central portion defines a longitudinal axis and the central portion is disposed between and interconnects the first apposition portion and the second apposition portion. In exemplary embodiments, at least one of the first flange members and at least one of the second flange members include a radius portion and a descending portion that extends longitudinally toward the central portion. At least one of the radius portions of the first flange members extends longitudinally beyond the first end and at least one of the radius portions of the second flange members extends longitudinally beyond the second end. In at least one embodiment, at least one of the first flange members or at least one of the second flange members further includes a horizontal portion that extends from the descending portion. The radius portions may extend from the first end or the second end of the central portion. Additionally, the descending portion may be a linearly descending portion. Further, the central portion may be configured to longitudinally extend and retract to maintain contact, over a range of tissue thicknesses, of the first and second apposition portions with the first and second tissue surfaces, respectively.

A third aspect of the invention relates to a method of implanting an anastomosis device in a patient that includes (1) positioning a delivery sheath containing the anastomosis device at a target location within the patient and (2) deploying the anastomosis device out from the delivery sheath such that at least one layer of tissue is between a first apposition portion and a second apposition portion of the device. The anastomosis device includes (1) an expandable frame having a first end, a second end, and a middle portion between the first end and the second end, (2) a first apposition portion including a plurality of first apposition members, each of the first apposition members extending toward the middle portion, and (3) a second apposition portion including a plurality of second apposition members extending toward the middle portion. A first portion of each of the first apposition members may be oriented at a first angle in relation to a surface of the middle portion and a second portion of each the first apposition members may be oriented at a second angle in relation to the surface of the middle portion. In exemplary embodiments, the first angle is acute and is less than the second angle. Also, a first portion of each of the second apposition members may be oriented at a third angle in relation to the surface of the middle portion and a second portion of each of the second apposition members may be oriented at a fourth angle in relation to the surface of the middle portion. In exemplary embodiments, the third angle is acute and is less than the fourth angle. In at least one exemplary embodiment, a tip portion of the plurality of first apposition members or the plurality of second apposition members is spaced apart from the tissue. In other exemplary embodiments, two layers of tissue are between the first apposition portion and the second apposition portion.

DESCRIPTION OF DRAWINGS

The accompanying drawings are included to provide a further understanding of the disclosure and are incorporated in and constitute a part of this specification, illustrate embodiments, and together with the description serve to explain the principles of the disclosure.

FIG. 10 is a perspective view of yet another exemplary anastomosis device in accordance with some embodiments;

FIG. 11 is an end view of the anastomosis device of FIG. 10;

FIG. 12 is an alternative embodiment of the anastomosis device of FIG. 10; and

DETAILED DESCRIPTION

Figure 1:
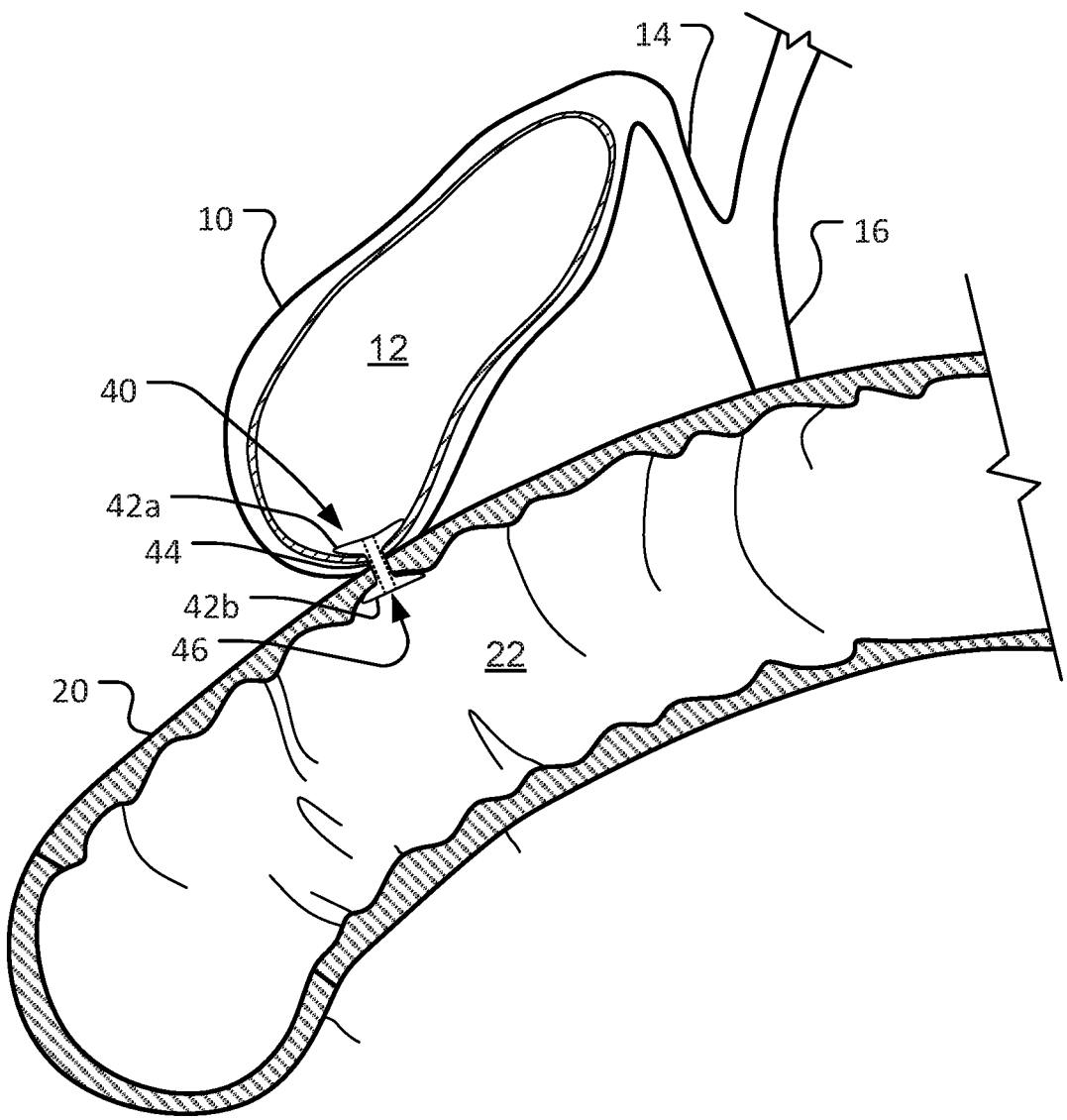
FIG. 1 is a cutaway perspective view of an exemplary anastomosis device, that has been implanted within a patient to act as a shunt between the patient's gallbladder and intestine according to some embodiments.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

The present invention is directed to implantable devices for connecting tissue layers, for example, to circumvent a conduit or organ blockage, such as by creating a direct passage between tissue structures (e.g. connecting a gallbladder and a portion of a gastrointestinal tract) to create an anastomosis that facilitates material flow therebetween. The devices described herein may be endoscopically deployable or deliverable via a catheter and may include self-expanding apposition mechanisms that facilitate a secure connection between the tissue structures (such a connection may also be referred to herein as a "shunt," "passageway," "shunt passageway," or "tunnel"). Such design features simplify implantation and reduce the likelihood of complications. In some embodiments, the devices provided herein are configured to be removable after implantation. As one example, the device is implanted and remains in place until the gallbladder and/or its associated ducts are cleared of blockages, after which the device is removed. In another example, the device remains implanted until the body grows a tissue-anastomosis around the device, and then the device is removed. In other embodiments, tissue ingrowth into and/or around the device permanently implants the device, and the device is not removed. The devices described herein can provide an alternative treatment for patients who are not suitable candidates for other types of treatments (e.g., gallbladder removal surgery) and/or to avoid known complications of other types of treatments (e.g., external biliary drainage).

This document refers to anastomosis devices in an exemplary fashion. That is, it should be understood that the inventive concepts disclosed in this document can also be applied to other types of devices. For example, this document also provides implantable devices that, in some embodiments, can be used for occluding tissue structures, organs, body conduits, blood vessels, the GI tract, and the like. For example, in some embodiments the devices provided herein can be used to occlude septal defects. In some embodiments, the devices provided herein can be used to occlude a patient's vasculature or GI tract. In some such embodiments, the device does not include a tunnel through the device. Rather, in some embodiments a covering material seals the device to inhibit, modulate, or substantially prevent material from flowing through the device.

Referring to FIG. 1, an exemplary anastomosis device 40 in accordance with one or more provided herein can be implanted in a patient to create a fluidic connection between two organs, spaces, tissue structures, conduits, and the like, and combinations thereof. For example, in the depicted implementation the anastomosis device 40 is connecting a gallbladder 10 (that defines an internal gallbladder space 12) with an intestine 20 (that defines an internal intestinal space 22). Hence, the anastomosis device 40 is acting as a fluidic shunt device between the internal gallbladder space 12 and the internal intestinal space 22. Such an implementation may provide a beneficial treatment to the patient when, for example, a flow blockage exists in the native anatomical conduits connecting the internal gallbladder space 12 and the internal intestinal space 22. For example, in some instances the patient may have one or more gallstones that cause a blockage of the patient's cystic duct 14 and/or common bile duct 16. In such a case, the anastomosis device 40 can provide a fluidic passageway such that bile from the gallbladder 10 can flow into the intestine 20. If not for the anastomosis device 40, when bile is blocked from flowing out of the gallbladder 10 cholecystitis (inflammation of the gallbladder 10) may result.

While the anastomosis devices provided herein can be used in some implementations to relieve or prevent cholecystitis as described above, it should be understood that the anastomosis devices provided herein can also be used in many other types of implementations within a patient. For example, the anastomosis devices provided herein can be used in conjunction with various body tissue structures and organs such as, but not limited to, stomachs, colons, small intestines, pancreases, blood vessels, bladders, kidneys, conduits, and the like.

In general, some embodiments of the anastomosis devices provided herein (of which anastomosis device 40 is one type of example), include a first tissue apposition portion 42a, a second tissue apposition portion 42b, and a central portion 44 between the first and second tissue apposition portions 42a and 42b. The central portion 44 defines a lumen 46 that extends longitudinally from a first end of the anastomosis device 40 to a second end of the device 40. The lumen 46 acts as a connection (e.g., a shunt passageway) between the internal gallbladder space 12 and the internal intestinal space 22, such that the internal gallbladder space 12 is in fluid communication with the internal intestinal space 22 via the anastomosis device 40.

Figure 2:
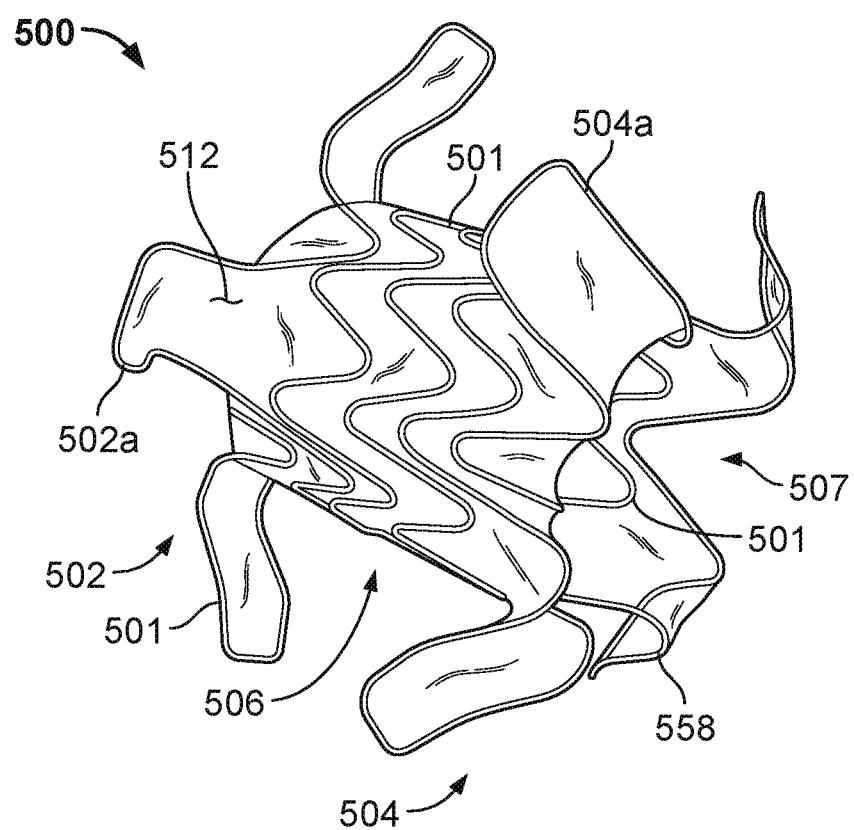
FIG. 2 is a perspective view of an exemplary anastomosis device in accordance with some embodiments.
Figure 3:
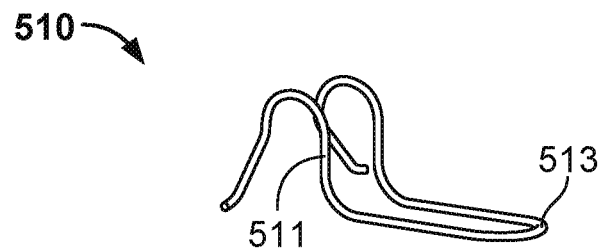
FIGS. 3-6 are perspective views of exemplary apposition members in accordance with some embodiments.
Figure 4:
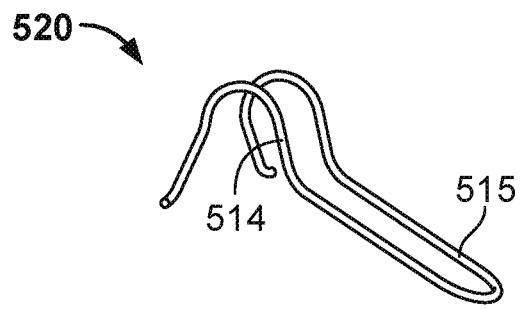
Figure 5:
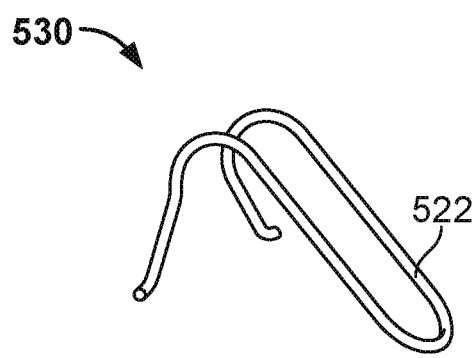
Figure 6:
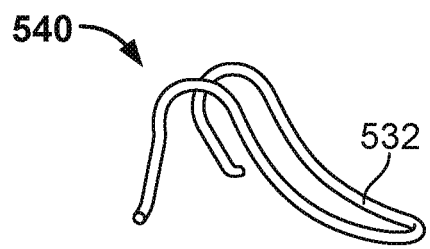

Referring to FIG. 2, an example anastomosis device 500 includes a framework of one or more elongate elements 501 that defines a first apposition portion 502, a second apposition portion 504, and a central portion 506 is depicted. The central portion 506 is disposed between and interconnects the first apposition portion 502 and the second apposition portion 504. In some embodiments, the central portion 506 is essentially cylindrical (although other geometries are also contemplated and are considered to be within the purview of the invention).

In some embodiments, a covering material 512 is disposed on at least some portions of the anastomosis device 500. As described further below, the covering material 512 can be disposed on some portions or on all of the first apposition portion 502, the second apposition portion 504, and/or the central portion 506. In some embodiments, portions of the first apposition portion 502, the second apposition portion 504, and/or the central portion 506 can remain free of the covering material 512.

In some embodiments, the central portion 506 defines a lumen 507 that extends between the first apposition portion 502 and the second apposition portion 504. In some implementations, the lumen 507 provides an anastomosis passageway or tunnel through which biological materials and/or fluids can pass. The device 500 is shown in an expanded configuration. The expanded configuration is the configuration that the device 500 naturally exhibits in the absence of external forces acting upon the device 500. In should be understood that when the anastomosis device 500 is implanted in a patient, the configuration of the device 500 may be somewhat different than shown because of the external forces from the patient's anatomy that are exerted on the device 500.

The anastomosis device 500 is shown in a deployed or expanded configuration. In some embodiments, the framework of the anastomosis device 500, as described further below, can be made of a variety of metallic shape memory materials and super-elastic alloys. Thus, in some embodiments the central portion 506 (and/or the apposition portions 502 and 504) can be configured to self-expand to the deployed configuration. In some embodiments, the central portion 506 is balloon expandable to the deployed configuration, or supplemental expansion forces can be applied to a self-expandable device by balloon dilation. The diameter of the central portion 506 can be made in any size as desired in order to suit the intended use and/or delivery system of the anastomosis device 500.

When the anastomosis device 500 is configured in its expanded deployed configuration as shown, the diameter of the central portion 506 increases to a deployed diameter. The diameter of the central portion 506 can be made in any dimension as desired in order to suit the intended use and/or delivery system of the anastomosis device 500. In some implementations, the deployed outer diameter of the central portion 506 is configured to at least partially anchor the device 500 via an interference fit with the tissue aperture in which the central portion 506 resides. Additionally, when the central portion 506 and the tissue aperture have an interference fit relationship, para-device leakage may be reduced or minimized. In such a case, leakage of the contents of the organs, conduits, and other types of tissue structures in which the anastomosis device 500 may be deployed can be substantially prevented. For example, when the anastomosis device 500 is used between a gallbladder and GI tract (e.g., refer to FIG. 1), leakage into the abdominal cavity can be substantially prevented.

In some implementations the deployed outer diameter of the central portion 506 is slightly less than the diameter of the tissue aperture in which the central portion 506 resides, and the apposition portions 502 and 504 compress the tissue to provide the migration resistance. In some embodiments, the fully expanded diameter of the central portion 506 is about 30 mm, or about 25 mm, or about 20 mm, or about 15 mm, or about 12 mm, or about 10 mm, or about 8 mm, or about 6 mm, or about 4 mm, and the like. In some embodiments, the fully expanded diameter of the central portion 506 is in a range between about 20 mm to about 30 mm, or about 15 mm to about 25 mm, or about 10 mm to about 20 mm, or about 5 mm to about 15 mm, or about 4 mm to about 8 mm, and the like.

The length of the central portion 506 can be made in any dimension as desired in order to suit the intended use and/or delivery system of the anastomosis device 500. For instance, in one exemplary embodiment the central portion 506 is about 13.5 mm in length and about 15 mm in diameter. In some embodiments, the length of the central portion 506 can be in a range from about 5 mm to about 10 mm, or about 8 mm to about 13 mm, or about 11 mm to about 16 mm, or about 14 mm to about 19 mm, or about 17 mm to about 22 mm, or greater than 22 mm.

In some embodiments, the anastomosis device 500 has a framework that comprises one or more elongate elements 501. In some embodiments, the one or more elongate elements 501 are wound into the framework configuration. In some embodiments, a single elongate element 501 is wound to form the framework of the anastomosis device 500. In some embodiments, two or more elongate elements 510 are cooperatively wound to form the framework of the anastomosis device 500.

In some embodiments, the framework of the first apposition portion 502, the second apposition portion 504, and the central portion 506 are formed of one or more elongate elements 501 made of materials such as, but not limited to, spring wire (e.g., L605 steel or stainless steels), shape memory alloy wire (e.g., nitinol or nitinol alloys), super-elastic alloy wire (e.g., nitinol or nitinol alloys), other suitable types of elongate elements or wires, or combinations thereof. In some embodiments, the first apposition portion 502, the second apposition portion 504, and the central portion 506 are formed from a precursor material that is cut to create the framework of elongate elements 501. In some such embodiments, the precursor material is a single piece of precursor material. In some embodiments, one or more elongate elements 501 are wound into a configuration to form the framework. In some embodiments, different types of elongate elements 501 are used at different locations of the first apposition portion 502, the second apposition portion 5, and/or the central portion 506. In some embodiments, the elongate elements 501 of the first apposition portion 502, the second apposition portion 504, and/or the central portion 506 (or portions thereof) may be constructed of polymeric materials.

Suitable materials for the elongate elements 501 of the anastomosis device 500 and/or other devices provided herein include a variety of metallic materials including alloys exhibiting, shape memory, elastic and super-elastic characteristics. Shape memory refers to the ability of a material to revert to an originally memorized shape after plastic deformation by heating above a critical temperature. Elasticity is the ability of a material to deform under load and return to its original shape when the load is released. Most metals will deform elastically up to a small amount of strain. Super-elasticity refers to the ability of a material to deform under strain to much larger degree than typical elastic alloys, without having this deformation become permanent. For example, the super-elastic materials included in the frames of some anastomosis device embodiments provided herein are able to withstand a significant amount of bending and flexing and then return to or substantially to the frame's original form without deformation.

In some embodiments, suitable elastic materials include various stainless steels which have been physically, chemically, and otherwise treated to produce a high springiness, metal alloys such as cobalt chrome alloys (e.g., ELGILOY™, MP35N, L605), platinum/tungsten alloys. Embodiments of shape memory and super-elastic alloys include the NiTi alloys, ternary shape memory alloys such as NiTiPt, NiTiCo, NiTiCr, or other shape memory alloys such as copper-based shape memory alloys. Additional materials could combine both shape memory and elastic alloys such as drawn filled tube where the outer layer is constructed of nitinol and the inner core is a radiopaque material such as platinum or tantalum. In this construct, the outer layer provides the super-elastic properties and the inner core remains elastic due to lower bending stresses.

In some embodiments, the elongate elements 501 used to construct the anastomosis device 500 and/or other devices provided herein can be treated in various ways to increase the radiopacity of the devices for enhanced radiographic visualization. In some embodiments, the devices are least partially a drawn-filled type of NiTi containing a different material at the core, such as a material with enhanced radiopacity. In some embodiments, the devices include a radiopaque cladding or plating on at least portions of the first apposition portion, the second apposition portion, and the central portion. In some embodiments, one or more radiopaque markers are attached to the devices. In some embodiments, the elongate elements and/or other portions of the devices provided herein are also visible via ultrasound, and may include portions with enhanced echogenicity.

In some embodiments, the materials and configuration of the anastomosis device 500 (and the other anastomosis device embodiments provided herein) allow the devices to be elastically crushed, folded, and/or collapsed into a low-profile delivery configuration for containment within a lumen for transcatheter or endoscopic/thorascopic delivery, and to self-expand to an operative size and configuration once positioned at a desired target site within a body and deployed from the lumen. For example, in the low-profile delivery configuration the anastomosis device 500 can be disposed within a delivery sheath that has about a 15 Fr. (5 mm) outer diameter. However, in some embodiments, sheaths that are smaller or larger than 15 Fr. can be used. For example, sheaths that have outer diameters of 6 Fr., 7 Fr., 8 Fr., 9 Fr., 10 Fr., 11 Fr., 12 Fr., 13 Fr., 14 Fr., 16 Fr., 17 Fr., 18 Fr., 19 Fr., 20 Fr., and larger than 20 Fr., can be used in some embodiments. While the anastomosis device 500 is configured in a collapsed delivery configuration, in some embodiments the framework of one or more elongate elements 501 is radially compressed such that the elongate elements 501 are forced to extend substantially parallel to axis of the central portion 506, and the diameter of the central portion 506 is crushed to become smaller.

The anastomosis device 500 also includes the covering material 512 (which may also be referred to herein as a "covering"). In some embodiments, the covering material 512 is disposed on at least some portions (or on all) of the first apposition portion 502, the second apposition portion 504, and the central portion 506. In some embodiments, some portions of the first apposition portion 502, the second apposition portion 504, and/or the central portion 506 are not covered by the covering material 512.

In some embodiments, the covering material 512 is generally fluid impermeable. That is, in some embodiments the covering material 512 is made of a material that inhibits or reduces passage of blood, bile and/or other bodily fluids and materials through the covering material 512 itself. In some embodiments, the covering material 512 has a material composition and configuration that inhibits or prevents tissue ingrowth and/or endothelialization or epithelialization into the covering material 512. Some such embodiments that are configured to inhibit or prevent tissue ingrowth and/or endothelialization can be more readily removed from the patient at a future date if so desired. In some embodiments, the covering material 512, or portions thereof, has a microporous structure that provides a tissue ingrowth scaffold for durable sealing and/or supplemental anchoring strength of the anastomosis device 500.

In some embodiments, the covering material 512 comprises a fluoropolymer, such as an expanded polytetrafluoroethylene (ePTFE) polymer, polyvinylidene fluoride (PVDF), or PVDA. In some embodiments, the covering material 512 comprises a polyester, a silicone, a urethane, biocompatible polymer(s), polyethylene terephthalate (e.g., Dacron®), bioabsorbable materials, copolymers, or combinations thereof. In some embodiments, the covering material 512 comprises a bioabsorbable web. In other embodiments, the bioabsorbable material may also provide an anti-migration feature by promoting attachment between the device 500 and tissue until the bioabsorbable material is absorbed.

In some embodiments, the covering material 512 (or portions thereof) is modified by one or more chemical or physical processes that enhance one or more properties of the material 512. For example, in some embodiments, a hydrophilic coating may be applied to the covering material 512 to improve the wettability and echo translucency of the material 512. In some embodiments, the covering material 512, or portions thereof, may be modified with chemical moieties that facilitate one or more of endothelial cell attachment, endothelial cell migration, endothelial cell proliferation, and resistance to or promotion of thrombosis. In some embodiments, the covering material 512, or portions thereof, may be modified to resist biofouling. In some embodiments, the covering material 512, or portions thereof, may be modified with one or more covalently attached drug substances (e.g., heparin, antibiotics, and the like) or impregnated with the one or more drug substances. The drug substances can be released in situ to promote healing, reduce tissue inflammation, reduce or inhibit infections, and to promote various other therapeutic treatments and outcomes. In some embodiments, the drug substance may be, but is not limited to a corticosteroid, a human growth factor, an anti-mitotic agent, an antithrombotic agent, a stem cell material, or dexamethasone sodium phosphate. In some embodiments, a pharmacological agent is delivered separately from the covering material 512 to the target site to promote tissue healing or tissue growth.

Coatings and treatments may be applied to the covering material 512 before or after the covering material 512 is joined or disposed on or around the framework of the anastomosis device 500. Additionally, one or both sides of the covering material 512, or portions thereof, may be coated. In some embodiments, certain coatings and/or treatments are applied to the covering material(s) 512 located on some portions of the anastomosis device 500, and other coatings and/or treatments are applied to the material(s) 512 located on other portions of the anastomosis device 500. In some embodiments, a combination of multiple coatings and/or treatments are applied to the covering material 512, or portions thereof. In some embodiments, certain portions of the covering material 512 are left uncoated and/or untreated. In some embodiments, the device 500 is fully or partially coated to facilitate or frustrate a biological reaction, such as, but not limited to, endothelial cell attachment, endothelial cell migration, endothelial cell proliferation, and resistance to or promotion of thrombosis.

In some embodiments, a first portion of the covering material 512 is formed of a first material and a second portion of the covering material 512 is formed of a second material that is different than the first material. In some embodiments, the covering material 512 is comprised of multiple layers of materials, which may be the same or different materials. In some embodiments, portions of the covering material 512 have one or more radiopaque markers attached thereto to enhance in vivo radiographic visualization of the anastomosis device 500, or one or more echogenic areas to enhance ultrasonic visibility.

In some embodiments, one or more portions of the covering material 512 are attached to the framework of the device 500, such as the central portion 506 and/or the apposition portions 502 and 504. The attachment can be accomplished by a variety of techniques such as, but not limited to, stitching the covering material 512 to the framework of the device 500, adhering the covering material 512 to the framework of the device 500, laminating multiple layers of the covering material 512 to encompass portions of the elongate members of the device 500, using clips or barbs, laminating multiple layers of the covering material together through openings in the framework of the device 500. In some embodiments, the covering material 512 is attached to the framework of the device 500 at a series of discrete locations, thereby facilitating the flexibility of the framework. In some embodiments, the covering material 512 is loosely attached to the framework of the device 500. It is to be appreciated that the covering material 512 may be attached to the framework using other techniques or combinations of techniques described herein.

In some embodiments, the framework of the device 500 (or portions thereof) is coated with a bonding agent (e.g., fluorinated ethylene propylene or other suitable adhesive) to facilitate attachment of the covering material 512 to the framework. Such adhesives may be applied to the framework using contact coating, powder coating, dip coating, spray coating, or any other appropriate means.

The covering material 512 can adapt to changes in the length and/or diameter of the central portion 506 in a variety of manners. In a first example, the covering material 512 can be elastic such that the covering material 512 can stretch to accommodate changes in the length and/or diameter of the device 500. In a second example, the covering material can include slackened material in the low-profile delivery configuration that becomes less slackened or totally unslackened when the device 500 is in the expanded configuration. In a third example, the covering material 512 can include folded portions (e.g., pleats) that are folded in the low-profile configuration and less folded or totally unfolded when the device 500 is in the expanded configuration. In some embodiments, combinations of such techniques, and/or other techniques can be used whereby the covering material 512 can adapt to changes in the length and/or diameter of the central portion 506.

The one or more elongate element(s) 501 of the central portion 506 can be configured in various ways to define a generally cylindrical framework. In the embodiment depicted in FIG. 2, the elongate element(s) 501 of the central portion 506 are wound circumferentially around the central portion 506. In addition to the circumferential winding, the elongate element(s) 501 can exhibit other winding paths, such as the wavy or serpentine path shown (e.g., approximately sinusoidal) and other paths. In the depicted embodiment, the winding path of the elongate element(s) 501 in the central portion 506 has eight apices per circumference, and an apical length of about 3.5 mm. In some embodiments, the elongate element(s) 501 of the central portion 506 can be made to have more or less than eight apices per circumference, and can be made to have an apical length of more than or less than 3.5 mm, as desired to suit a particular application. For example, in some embodiments the elongate element(s) 501 of the central portion 506 can be made to have three, four, five, six, seven, nine, ten, eleven, twelve, thirteen, fourteen, fifteen, sixteen, or more than sixteen apices per circumference. In some embodiments, the elongate element(s) 501 of the central portion 506 can be made to have an apical length in a range of about 1 mm to about 2 mm, or about 2 mm to about 3 mm, or about 3 mm to about 4 mm, or about 4 mm to about 5 mm, or about 5 mm to about 6 mm, or about 6 mm to about 7 mm, or greater than 7 mm.

In some embodiments, the apposition portions 502 and 504 include one or more flange components 502a and 504a, respectively. Such flange components (e.g., flange components 502a and 504a) may also be referred to herein as "fins," "petals," or "fingers." The flange components 502a and 504a are configured to contact tissues and to exert an apposition pressure thereto. While the depicted embodiment includes four flange components 502a and four flange components 504a, other quantities of flange components 502a and 504a can be included. For example, in some embodiments one, two, three, five, six, seven, eight, or more than eight flange components 502a and/or 504a may be included. In some embodiments, unequal numbers of flange components 502a and flange components 504a are included.

The flange components 502a and 504a can be configured to exert a predictable and desired apposition force when in contact with tissue. For example, the material(s), the diameter, and other properties of the elongate element can be selected to attain a desired apposition force. Elongate elements (e.g., nitinol elongate members) can be made to have a particular diameter as desired. Elongate elements made of other suitable materials and with larger or smaller diameters can be selected as desired. The geometry of the flange components 502a and 504a can also affect the apposition force exerted by the flange components 502a and 504a. That is, geometry aspects such as, but not limited to, the length, width, radii, angles, arcs (and the like) of the flange components 502a and/or 504a can be selected to attain a desired apposition force.

In some embodiments, the flange components 502a and 504a can be configured to have an offset orientation between the opposite end portions of the anastomosis device 500. That is, the axes of one or more of the individual flange components 502a may be offset (e.g., skewed, or out of alignment) from the axes of one or more of the individual flange components 504a. In some such embodiments, some or all of the flange components 502a and 504a can be configured to cross each other (e.g., overlap each other in an interposing arrangement). In some such embodiments, some or all of the flange components 502a and 504a may be offset from each other but not crossing each other. However, in some embodiments the axes of one or more of the individual flange components 502a may be generally in alignment (e.g., substantially parallel) with the axes of one or more of the individual flange components 504a. In some such embodiments, some or all of the flange components 502a and 504a can be configured to abut each other. In some such embodiments, some or all of the flange components 502a and 504a may be in alignment with each other but not abutting each other.

In some embodiments, one or more of the flange components 502a and/or 504a may vary in configuration in comparison to one or more others of the flange components 502a and/or 504a. For example, the flange components 502a can protrude farther towards the central portion 506 than the flange components 504a (or vice versa). Or, one or more of the flange components 502a or 504a can protrude farther towards the central portion 506 than others of the flange components 502a or 504a respectively.

In some embodiments, one or more of the flange components 502a and/or 504a may have two or more portions with differing curvatures (radii). For example, in the depicted embodiment, at least some of the flange components 502a and/or 504a extend from the central portion 506 at a first radius, and then straighten to a generally linear portion, and then curve along a second radius after which the flange components 502a and/or 504a terminate. In some embodiments, the first radius is unequal to the second radius. In some embodiments, the first and second radii are curved in opposite directions from each other.

In some embodiments, a radius 558 of the flange components 502a and 504a protrudes beyond the central portion 506 of the device. Therefore, the force applied by the flange components 502a and 504a may push some tissue into the radius 558, thereby making a longer and potentially stronger or less leak-prone anastomosis. In some embodiments, the radius 558 of curvature is determined by the allowed strain of the nitinol material when loaded into a delivery system (e.g., sheath). For example, in some embodiments a strain of about 6.4% may result. However, other strain levels of less than or more than about 6.4% are used in some embodiments.

In some implementations, including multiple flange components 502a and 504a may tend to reduce the potential for causing tissue ischemia. In some embodiments, individual flange components 502a are configured differently from each other, and/or individual flange components 504a are configured differently from each other. In some embodiments, the flange components 502a and 504a can remain discrete from each other (as shown), or in some embodiments the flange components 502a and 504a are interconnected to each other by, for example, the covering 512. In some embodiments, the flange components 502a and 504a can oppose or not oppose each other, can crisscross over each other, can have different geometries (e.g., lengths, widths, angles, radii, shapes, etc.). All combinations of such design features can be combined to create anastomosis devices of a wide variety of configurations. In some embodiments, one or both of the flange components 502a and 504a protrude from the central portion 506 at an axial orientation and shape to achieve a specific desired apposition pressure on the tissue.

Figure 7:
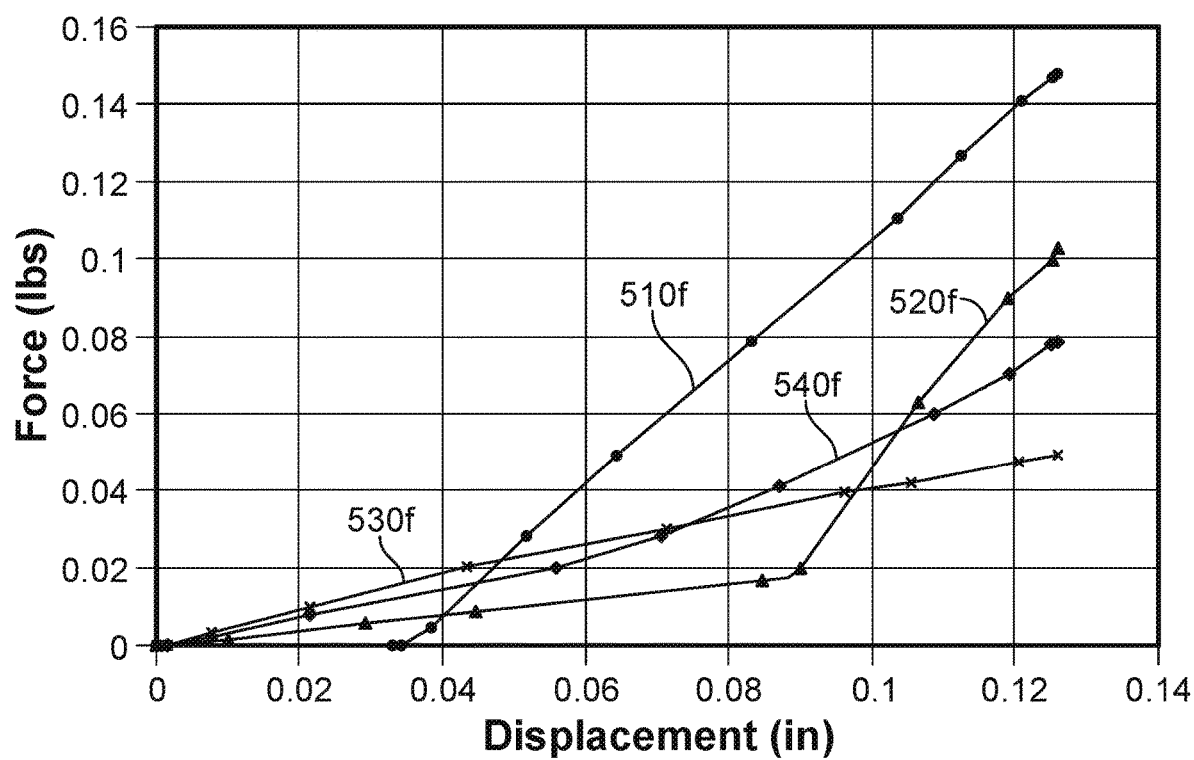
FIG. 7 is graphical illustration showing the relationship between force and displacement for each of the apposition members shown in FIGS. 3-6.

In some embodiments, one or more of the shape of the flange components, the number of flange components, the elongate element size, and the tissue thickness are factors that are selectable to achieve a specific force profile vs. displacement. For example, referring to FIGS. 3-6, various exemplary flange component designs 510, 520, 530, and 540 are shown. The free ends shown in FIGS. 3-6 are where the flange components design 510, 520, 530, and 540 would extend from the device body (e.g., anastomosis device 500). The force vs. displacement curves for each is shown in FIG. 7.

The exemplary flange component 510 includes a sharply descending region 511 extending to the edge of the central portion (not shown), and a substantially horizontal region 513 extending away from the device. The exemplary flange component 520 includes a moderately sharp descending region 514 connected to and a sloping region 515 extending away from the device. The exemplary flange component 520 includes a linearly descending region 522 extending away from the device. The exemplary flange component 530 includes a gradual sloping curved region 532 extending away from the device. In some embodiments, one or more regions of the flange components longitudinally extend towards the central portion of the device of which the flange components are part of (e.g., towards central portion 506 of anastomosis device 500).

Particular flange component force vs. displacement profiles (e.g., flange components 510, 520, 530, and 540) may be advantageous for achieving a desired apposition pressure and/or other performance characteristics. For example, referring to FIG. 7, a graph of force vs. displacement shows the apposition force that can be applied by each flange component 510 (510f), 520 (520f), 530 (530f), and 540 (540f). The force vs. displacement profile of flange component 510 can include a steep linear slope, as shown by 510f. Curve 510f may be of particular benefit if the organs to be apposed are not close together. The linear and quickly increasing force would resist separation of the organs. In some embodiments, the force vs. displacement profile of flange component 520 can include a shallow linear slope that abruptly changes to a steep linear slope (520f). Curve 520f may be of particular benefit for creating high apposition force during the initial healing phase while the anastomosis is being created. During this time the tissue may be thicker and inflamed utilizing the steep linear profile of 520f. As the tissue inflammation and resulting tissue thickness reduced, the shallow part of curve 520f would be employed helping to avoid necrosis of the tissue. The force vs. displacement profile of flange component 530 produces a shallow linear slope (530f). Curve 530f provides a shallow linear increase in force with respect to displacement and may be particularly useful for tissue that is considered friable and prone to perforation. In other embodiments, the force vs. displacement profile of flange component 540 can include a continuously increasing slope (540f). Such variations of flange components (and other variations also contemplated within the scope of this disclosure) can be selected for a particular application as desired. For example, the force vs. displacement curve achieved by flange component 540 may be advantageous in particular applications because the curve smoothly increases and the design allows for a broad area of contact over a large range of displacement.

Figure 8:
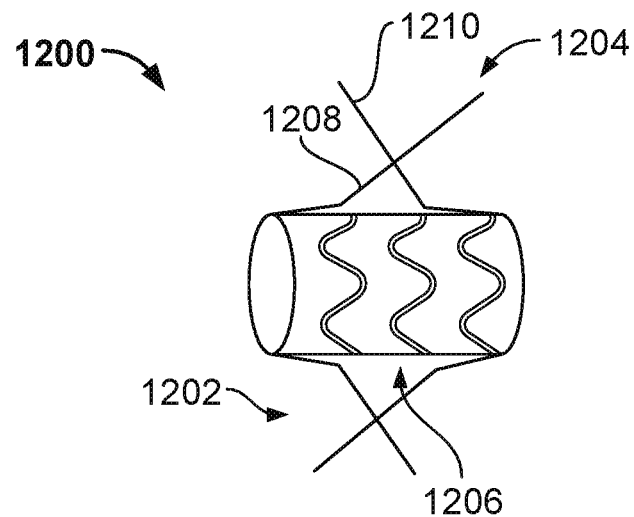
FIG. 8 is a schematic illustration of another exemplary anastomosis device in accordance with some embodiments.
Figure 9:
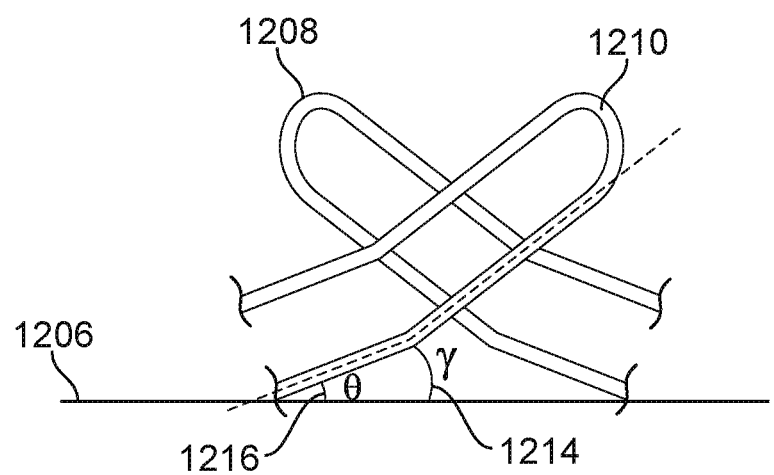
FIG. 9 is a schematic illustration of exemplary apposition members in accordance with some embodiments.

FIGS. 8 and 9 illustrate another example anastomosis device 1200. Anastomosis device 1200 is an example variation of the anastomosis device 500 described above. In particular, the anastomosis device 1200 has first and second apposition portions 1202 and 1204 that are designed differently than the first and second apposition portions 502 and 504 of anastomosis device 500. As described further below, the one or more apposition members 1208 and 1210 that make up the first and second apposition portions 1202 and 1204 can be configured to provide functional properties that are desirable in some implementations.

In some embodiments, the framework of the device 1200 or any portion thereof can comprise elongate elements such as a spring wire (e.g., L605 steel or stainless steels), shape memory alloy wire (e.g., nitinol or nitinol alloys), superelastic alloy wire (e.g., nitinol or nitinol alloys), other suitable types of wire, or combinations thereof. In the depicted embodiment of device 1200, the framework includes an elongate element that is formed by winding, for example. In some embodiments, different types of wires are used at different locations of the device 1200. Alternatively, device 1200 or portions thereof can be formed from the same piece of precursor material that is cut to create the elongate element framework structure as desired. In some embodiments, the device 1200 or portions thereof may be constructed of polymeric materials. The device 1200 is shown with a covering material, as described above. It should be understood that anastomosis device 1200 can be constructed using any of the materials and techniques described in reference to any and all other anastomosis devices described herein.

The central portion 1206 of the device can be constructed to have a tailored radial strength by, for example, varying the elongate element's sine wave amplitude, angle, number of apices per row, number of rows, wire diameter, and by selecting (or not selecting) a covering material. For anastomosis device applications, the radial strength of the central portion 1206 may be designed to resist circumferential loading from the surrounding tissue. Therefore, in some embodiments the radial strength of the central portion 1206 is configured to facilitate remodeling of the tissue external to the central portion 1206 to become approximate in size to the outer diameter of the central portion 1206. When the anastomosis device 1200 (and the other anastomosis devices provided herein) is implanted to form an anastomosis, the radial strength of the central portion 1206 provides resistance to the hoop force applied by the surrounding tissue. Therefore, an anastomosis device with strong radial strength in the central portion (e.g., central portion 1206) will substantially maintain an open lumen at a desired dimension. In addition, a device with strong radial strength can advantageously act as a scaffold for tissue to grow around the device.

In some embodiments, the materials and configuration of the anastomosis device 1200 allow the device 1200 to be elastically crushed, folded, and/or collapsed into a low-profile configuration for containment within a lumen for transcatheter or endoscopic/thorascopic delivery, and to self-expand to an operative size and configuration once positioned at a desired target site within a body and deployed from the lumen.

The first apposition portion 1202 and the second apposition portion 1204 are configured to engage one or more layers of tissue between the first and second apposition portions 1202 and 1204, and to provide apposition forces against the tissue surfaces. The apposition forces provided by the first and second apposition portions 1202 and 1204 can facilitate fixation of the device 1200 to the tissue, and provide migration resistance such that the device 1200 can reliably remain positioned at a target site in a patient as desired.

The first apposition portion 1202 and the second apposition portion 1204 each include one or more apposition members 1208 and 1210 respectively. The anastomosis device 1200 can be configured in a collapsed low-profile delivery configuration in which the apposition members 1208 and 1210 are radially compressed such that they extend substantially parallel to the longitudinal axis of the device. In the deployed or expanded configuration, the apposition members 1208 and 1210 protrude outwardly from the central portion 1206.

In some embodiments, at least one of the apposition members 1208 and/or 1210 is orientated to have a first angle 1216 in relation to the central portion 1206 and to have a second angle 1214 in relation to the central portion 1206 (as shown in FIG. 9). In other words, in some embodiments at least one apposition member 1208 and/or 1210 is non-planar. In the depicted embodiment the apposition member 1210 is orientated at a first angle 1216 in relation to the central portion 1206, and the apposition member 1210 is also oriented at a second angle 1214 in relation to the central portion 1206. In some embodiments, the first angle 1216 is a shallow angle. For example, in some embodiments the angle 1216 is acute, e.g., less than about 90°, or less than about 75°, or less than about 60°, or less than about 45°, or less than about 30°, or less than about 25°, or less than about 20°, or less than about 15°, or less than about 10°, or less than about 5°. In some embodiments, the angle 1216 is between about 15° and about 20°, or between about 10° and about 30°, or between about 5° and about 45°.

Because in some embodiments the angle 1216 is relatively shallow, and because the apposition member 1210 extends towards the central portion 1206, a portion of the apposition member 1210 is therefore orientated relatively close to the access location (i.e., the incision location in which the anastomosis device 1200 will be deployed). Hence, this configuration facilitates an effective and sustainable apposition of tissue.

In some embodiments, the second angle 1214 is a larger angle than the first angle 1216. For example, in some embodiments the angle 1214 is greater than about 90°, less than about 45°, less than about 25°, less than about 20°, less than about 15°, less than about 10°, or less than about 5°. In some embodiments, the angle 1214 is between about 30° and about 40°, or about 20° and about 45°, or about 30° and about 50°, or about 40° and about 60°, or about 50° and about 70°, or about 60° and about 80°, or about 70° and about 90°. In some embodiments the second angle 1214 is larger than the first angle 1216 such that a portion of the apposition member is orientated farther away from the access location. While, the shallow angle of the first angle 1216 permits tissue contact resulting in apposition force near the access location, the larger angle of the second angle 1214 perm its tissue contact away from the access location, providing anti-migration forces to keep the device 1200 in place. Moreover, in some embodiments the larger angle of the second angle 1214 permits the terminal ends of the apposition members 1208 and/or 1210 to be out of contact with tissue in situ. In some such implementations, by having fins pointing away from the apposed tissue, the potential for tissue over-growth on fins can be delayed or avoided. By delaying or avoiding tissue overgrowth the device can be easily removed when/if needed. In some embodiments, a single apposition member of this design can provide the benefits that are associated with having dual length apposition members.

In some embodiments, the apposition members 1208 and 1210 are in axial alignment with each other such that the positions of the apposition members 1208 and 1210 around the periphery of the central portion 1206 longitudinally coincide with each other. In some embodiments, the apposition members 1208 and 1210 are out or axial alignment with each other such that the positions of the apposition members 1208 and 1210 around the periphery of the central portion 1206 do not longitudinally coincide with each other. In some such embodiments, one or more of the apposition members 1208 of the first apposition portion 1202 longitudinally overlap (e.g., criss-crossed in an interposing arrangement) with one or more of the apposition members 1210 of the second apposition portion 1204, as depicted in FIGS. 8 and 9. In some embodiments, some or all of the apposition members 1208 and 1210 may be offset from each other, or in alignment with each other, while not crossing each other.

In some embodiments, some or all of the apposition members 1208 and 1210 may be in alignment with each other and abutting each other.

Referring to FIGS. 10-12, an anastomosis device 1300 is shown having a central portion 1306 that is interchangeable with any other central portion described herein, a first apposition portion 1302, and a second apposition portion 1304. In some embodiments, the framework of device 1300 or any portion thereof can comprise one or more elongate elements such as a spring wire (e.g., L605 steel or stainless steels), shape memory alloy wire (e.g., nitinol or nitinol alloys), super-elastic alloy wire (e.g., nitinol or nitinol alloys), other suitable types of wire, or combinations thereof (as described above in reference to elongate element 501).

In the depicted embodiment of device 1300, the framework is comprised of a single elongate element that is formed by winding and shape-setting, for example. In some embodiments, different types of elongate elements are used at different locations of the device 1300. Alternatively, the anastomosis device 1300 (or portions thereof) can be formed from the same piece of precursor material that is cut and expanded to create the elongate element framework structure as desired. In some embodiments, the device 1300 (or portions thereof) may be constructed of polymeric materials. It should be understood that anastomosis device 1300 can be constructed using any of the materials and techniques described in reference to any and all other anastomosis devices described herein.

In some embodiments, the framework of the central portion 1306 can be configured such that the central portion 1306 is longitudinally extendable. For example, in the depicted embodiment of anastomosis device 1300 the framework of the central portion 1306 includes serpentine-wound portions that allow for longitudinal extension and retraction (like a spring). Accordingly, the longitudinal length of the central portion 1306 can self-adjust based on in vivo loading forces. This feature can be advantageous, for example, in maintaining apposition when the tissue thickness changes during the healing process (e.g., in at least some cases of acute cholecystitis). It should be understood that this feature can be incorporated into any of the device embodiments described herein.

The device 1300 may include a covering material 1312. In some embodiments, the covering 1312 is made of stretchable (elastic-like) material that can have a high percentage of recoverable strain (e.g., recoverable strain in the magnitude of 100s of percentage per unit length). Some embodiments of such covering materials may include, but are not limited to, pure silicone, urethane material, or such materials that are imbibed in or laminated to other materials including, but not limited to, fluoropolymers such as ePTFE. In some embodiments, the covering material 1312 is as described herein (e.g., similar or identical to covering material 512).

The first apposition portion 1302 and the second apposition portion 1304 are configured to engage one or more layers of tissue between the first and second apposition portions 1302 and 1304, and to provide apposition forces against the tissue surfaces. The apposition forces provided by the first and second apposition portions 1302 and 1304 can facilitate attachment of the device 1300 to the tissue and provide displacement resistance such that the device 1300 can reliably remain positioned at a target site in a patient as desired.

The first apposition portion 1302 and the second apposition portion 1304 each include one or more apposition members 1302a or 1302a' and 1304a or 1304a' (also referred to herein as anchor members, fins, flange portions, petals, etc.). In some embodiments, the apposition members 1302a and 1304a are bare elongate elements (without a covering). In some embodiments, the apposition members 1302a' and 1304a' have the covering material 1312 disposed on at least some areas of their elongate elements.

In some embodiments, one or more of the apposition members 1302a or 1302a' and/or 1304a or 1304a' have different configurations (e.g., geometries, lengths, widths, shapes, etc.) than one or more other apposition members 1302a or 1302a' and/or 1304a or 1304d.

In some embodiments, the materials of the anastomosis device 1300 allow the device 1300 to be elastically crushed, folded, and/or collapsed into a low-profile configuration for containment within a lumen for transcatheter or endoscopic/thorascopic delivery, and to self-expand to an operative size and configuration once positioned at a desired target site within a body and deployed from the lumen. For example, the anastomosis device 1300 can be configured in a collapsed delivery configuration in which the framework is compressed to a low-profile such that the apposition members 1302a or 1302a' and 1304a or 1304a' extend substantially parallel to the longitudinal axis of the device 1300. In the deployed or expanded configuration, the apposition members 1302a or 1302a' and 1304a or 1304a' extend outwardly from the central portion 1306.

In some embodiments, the lengths of some of the apposition members 1302a or 1302a' and 1304a or 1304a' are dissimilar to provide both sufficient apposition forces near the periphery of the access location or hole where access is created, and anti-migration forces farther away therefrom. For example, in some embodiments one or more of the apposition members 1302a or 1302a' is longer than one or more of the apposition members 1304a or 1304d. In some embodiments, the apposition members 1302a or 1302a' and/or 1304a or 1304a' have varying lengths and are alternated, or arranged around the periphery of the first apposition portion 1302 and/or the second apposition portion 1304 in a pattern. In some embodiments, the apposition members 1302a or 1302a' and/or 1304a or 1304a' within each apposition portion 1102 and/or 1104 are uniform in length.

In some embodiments, the apposition members 1302a or 1302a' and/or 1304a or 1304a' have lengths that are selected based at least in part on the size of tissue structures that the device 1300 is to be implanted into. For example, if a first tissue structure generally includes smaller geometry than the second tissue structure, having differing lengths of the apposition members 1302a or 1302a' versus 1304a or 1304a' can be advantageous. In this example, the apposition portion entering the smaller tissue structure may beneficially have apposition members with a shorter length, while longer apposition members may be better-suited in the larger tissue structure. In some such implementations, the shorter length apposition members provide an appropriate fit for the smaller tissue structure thus ensuring sufficient tissue contact necessary for an anastomosis device, while the longer apposition members provide anti-migratory forces that help to retain the device in place. In some embodiments, such short and long apposition members 1302a or 1302a' and/or 1304a or 1304a' are staggered, nested, or separated around a periphery of a particular apposition portion 1302 and/or 1304.

The anastomosis device 1300 (and other embodiments that share design features of the anastomosis device 1300) can exhibit the following advantages. Having varying lengths of apposition members 1302a or 1302a' and/or 1304a or 1304a' can provide apposition at various target tissue locations. Having one or more such specific apposition zones may minimize or eliminate leakage of fluid or other contents that pass through the device lumen. Discrete apposition members 1302*a* or 1302*a*' and/or 1304*a* or 1304*a*' that move independently of each other can provide advantageous apposition member conformability to non-planar tissue topography. Better conformability can minimize tissue injury especially when used in a diseased tissue bed. The flexible discrete design of the apposition members 1302*a* or 1302*a*' and/or 1304*a* or 1304*a*' can facilitate device 1300 removal by folding the apposition members 1302*a* or 1302*a*' and/or 1304*a* or 1304*a*' parallel to the lumen of the device 1300. This flexibility of the apposition members 1302*a* or 1302*a*' and/or 1304*a* or 1304*a*' may help to minimize tissue injury during removal of the anastomosis device 1300.

Figure 13:
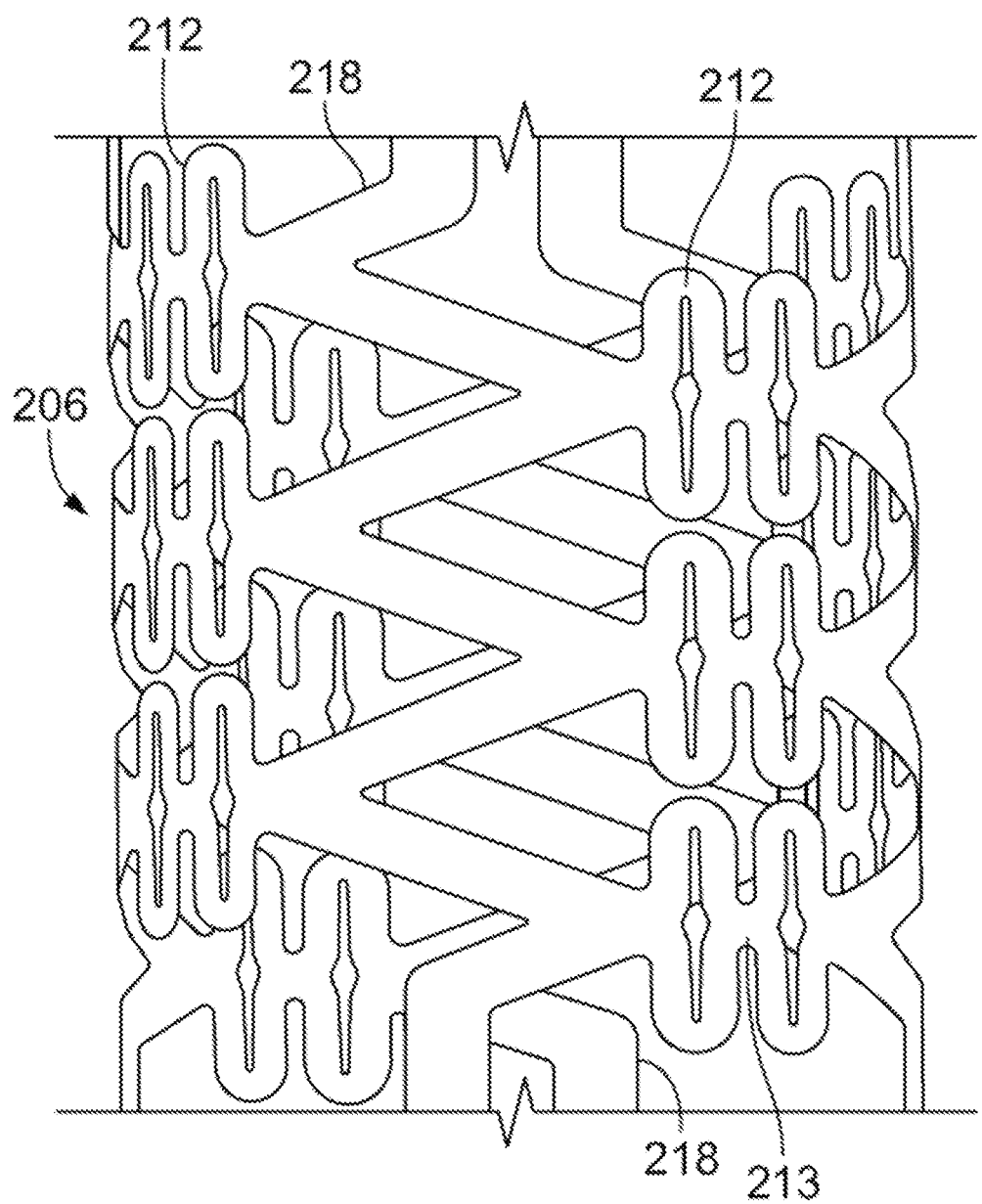
FIG. 13 is a side view of a central portion of another anastomosis device that includes expansion members in accordance with some embodiments.

Referring to FIG. 13, another example central portion 206 can be included as part of any the anastomosis devices provided herein. As with the central portions 506, 1206, and 1306, the central portion 206 is comprised of a framework of one or more elongate elements. For enhanced visibility, the central portion 206 is shown without a covering material, however the covering material(s) described elsewhere herein can be applied to the central portion 206 in some embodiments. In this example, the central portion 206 is shown in an undeployed or low-profile delivery configuration. When deployed in a patient, the central portion 206 can self-expand or be forced to expand to an expanded configuration.

The one or more elongate elements of the central portion 206 can be constructed from the same types of materials and can be constructed using the same types of techniques as described above in reference to the elongate elements of anastomosis device 500. In some embodiments, the central portion 210 is formed by one or more wound wires. In some embodiments, the central portion 206 is formed from a unitary piece of precursor material that is cut to create the elongate element framework structure as desired. In some such embodiments, the precursor material is a tube (e.g., a nitinol tube) that is laser cut to form the desired elongate element framework structure. In some such embodiments, the precursor material is a sheet (e.g., a nitinol sheet) that is laser cut to form the desired elongate element framework structure. In some embodiments, different types of elongate elements are used at different portions of the central portion 206. For example, in some embodiments the central portion 206 or portions thereof may be constructed of polymeric materials.

The central portion 206 includes one or more axial adjustment members 218 extending along the longitudinal axis of the central portion 206. The axial adjustment members 218 allow the axial length (also referred to herein as "longitudinal length") of the central portion 206 to elastically extend or contract (as described above in reference to the framework of the central portion 1306 of anastomosis device 1300).

The central portion 206 also includes one or more cells 212. In some embodiments, the one or more cells 212 interconnect the axial adjustment members 218. The cells 212 allow for the radial expansion and contraction of the central portion 206, and provide radial strength to the device to maintain its shape/size while resisting external compression forces. During radial expansion of the central portion 206, the cells 212 expand in the circumferential direction and collapse in the longitudinal direction. While the cells 212 are shown as having a diamond-like shape, other geometries may be used. In the depicted embodiment, pairs of cells 212 are interconnected to each other in the circumferential direction by a bridge member 213. However, in some embodiments a single cell 212, or more than two cells 212, may be included (rather than the pair shown).

In some embodiments, the cells 212 are unconnected to adjacent cells 212 along the longitudinal axis of the central portion 206. As such, the cells 212 connecting to the axial adjustment members 218 do not substantially constrain the axial expansion or contraction of the axial adjustment members 218 and/or the central portion 206. In some embodiments, the cells 212 provide radial strength to the central portion 206. That is, in some embodiments the cells 212 tend to self-expand into an expanded configuration. Such self-expansion can provide radial forces from the central portion 206 to the tissues in that are contacted by the central portion 206.

In some embodiments, axial length of the central portion 206 is adjusted before or during deployment, e.g., by a clinician to accommodate differences in tissue thicknesses. In other embodiments, the axial adjustment member 218 self-responds to mechanical forces exerted on the deployed anastomosis device in situ. For example, the axial adjustment member 218 permits the axial length of the device to dynamically adjust during the healing process (as described above in reference to central portion 1306).

The anastomosis devices provided herein are deployable to a target site within a patient using one or more catheters, delivery sheaths, and other suitable devices and techniques. In some implementations, the anastomosis devices provided herein are deployable using an endoscopic or laparoscopic approach.

It should be understood that one or more design features of the anastomosis devices provided herein can be combined with other features of other anastomosis devices provided herein. In effect, hybrid designs that combine various features from two or more of the anastomosis device designs provided herein can be created, and are within the scope of this disclosure.

In some such embodiments, the device does not include a tunnel or central aperture through the device.

In some embodiments the devices provided herein can be used for sealing or anchoring a heart valve implant. A heart valve implant enables one-way flow of blood from a heart chamber and usually has a first inflow end and a second outflow end. The contractions of the heart cause flow of blood through the valve from the inflow end to the outflow end. Between the inflow and outflow ends, a valve assembly within the heart valve implant provides for one way flow, opening to allow flow from the inflow to the outflow end when the pressure of the blood is higher on the inflow end, and closing to prevent flow when the pressure on the outflow end is higher than the inflow end. In some embodiments, the device includes a tunnel or central aperture through the device with apposition portions to anchor a valve assembly and seal against backward flow. A valve assembly can be attached in the tunnel or central aperture. The apposition portions of the device can be configured to be highly conformable to the topography of the heart chambers or blood vessels, and compliant with the beating movements of the heart. In some embodiments, a covering material is configured to allow flow through a valve assembly in the tunnel or aperture while preventing flow around the apposition portions.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A medical device comprising:
a frame comprising at least one elongate member;
a first apposition portion including at least a first portion of the elongate member defining a plurality of first apposition petals;
a second apposition portion including at least a second portion of the elongate member defining a plurality of second apposition petals;
a central portion including at least a third portion of the elongate member, the third portion of the elongate member including a serpentine shape configured to facilitate longitudinal extension and retraction, the third portion of the elongate member being longitudinally extendable, wherein the serpentine shape is defined along a longitudinal length of the third portion and positioned along only a portion of a circumference of the third portion to define a sinusoidal shape; and
a covering material disposed on at least some portions of the first apposition portion, the second apposition portion, and the central portion and forming a substantially cylindrical lumen within the central portion, wherein the covering material is elastic and configured to stretch to accommodate changes in length or diameter of the central portion.

2. The device of claim 1, wherein the at least one of the first portion of the elongate member, the second portion of the elongate member, and the third portion of the elongate member is different than another of the first portion of the elongate member, the second portion of the elongate member, and the third portion of the elongate member.

3. The device of claim 1, wherein at least portions of the first apposition portion and the second apposition portion are uncovered by the covering material.

4. The device of claim 1, wherein a deployed outer diameter of the central portion is slightly less than a diameter of a tissue aperture in which the central portion is configured to deploy.

5. The device of claim 4, wherein the first apposition portion and the second apposition portion are configured to compress opposing tissue sides to facilitate migration resistance.

6. The device of claim 1, wherein one or more of the first apposition petals are offset from one or more of the second apposition petals.

7. The device of claim 6, wherein an axes of the one or more of the first apposition petals are offset from an axes of one or more of the second apposition petals.

8. The device of claim 7, wherein at least a portion of the one or more of the first apposition petals overlap or cross a portion of another of the one or more of the second apposition petals.

9. The medical device of claim 1, wherein the third portion of the elongate member includes serpentine-wound portions.

10. The medical device of claim 9, wherein the serpentine-wound portions allow for longitudinal extension and retraction of the third portion of the elongate member.

11. A medical device comprising:
a frame comprising at least one elongate member;
a first apposition portion including at least a first portion of the elongate member defining a plurality of first apposition petals;
a second apposition portion including at least a second portion of the elongate member defining a plurality of second apposition petals;
a central portion including at least a third portion of the elongate member, the third portion of the elongate member being longitudinally self-adjustable in response to in vivo loading forces, the third portion including a serpentine shape configured to facilitate longitudinal extension and retraction,
wherein the serpentine shape extends around only a portion of a circumference of the third portion to define a sinusoidal shape; and
a covering material disposed on at least some portions of the first apposition portion, the second apposition portion, and the central portion and forming a substantially cylindrical lumen within the central portion, wherein the covering material is elastic and configured to stretch to accommodate changes in length or diameter of the central portion.

12. The medical device of claim 11, wherein the covering material is slack when the frame is in a low-profile delivery configuration.

13. A medical device comprising:
an elongate member defining a frame, the frame including:
a first apposition portion including at least a first portion of the elongate member defining a plurality of first apposition petals;
a second apposition portion including at least a second portion of the elongate member defining a plurality of second apposition petals; and
a central portion including at least a third portion of the elongate member, the third portion of the elongate member being longitudinally extendable, the third portion including a serpentine shape configured to facilitate longitudinal extension and retraction, wherein the serpentine shape extends along a longitudinal axis around only a portion of a circumference of the third portion to define a sinusoidal shape; and
a covering material disposed on at least some portions of the first apposition portion, the second apposition portion, and the central portion and farming a substantially cylindrical lumen within the central portion, wherein the covering material is elastic and configured to stretch to accommodate changes in length or diameter of the central portion.

* * * * *